(12) United States Patent
Saleh

(10) Patent No.: US 6,562,996 B2
(45) Date of Patent: May 13, 2003

(54) ALKYL AROMATIC ALDEHYDES

(75) Inventor: Ramzi Yanni Saleh, Baton Rouge, LA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 09/933,519

(22) Filed: Aug. 20, 2001

(65) Prior Publication Data

US 2002/0068841 A1 Jun. 6, 2002

Related U.S. Application Data

(63) Continuation-in-part of application No. 09/393,664, filed on Sep. 10, 1999, now Pat. No. 6,303,827.
(60) Provisional application No. 60/099,783, filed on Sep. 10, 1998.

(51) Int. Cl.[7] ................. C07C 63/00; C07C 63/14; C07C 51/10; C07C 51/16; C07C 45/00
(52) U.S. Cl. ............ 562/405; 562/406; 562/409; 562/413; 562/480; 568/425
(58) Field of Search ................. 568/425, 428; 562/405, 406, 409, 480, 413

(56) References Cited

U.S. PATENT DOCUMENTS

| | | | |
|---|---|---|---|
| 2,485,237 A | 10/1949 | Gresham et al. | 260/599 |
| 3,284,508 A | 11/1966 | Gray et al. | 260/599 |
| 3,539,650 A | 11/1970 | Amir | 260/674 |
| 3,644,552 A | 2/1972 | Notaro et al. | 260/674 |
| 3,856,832 A | 12/1974 | Ethyl Corp. | 260/410 |
| 3,948,998 A | 4/1976 | Fujiyama et al. | 260/599 |
| 4,218,403 A | 8/1980 | Vanderpool | 568/428 |
| 4,368,336 A * | 1/1983 | Fujiyama et al. | 568/428 |
| 4,518,798 A | 5/1985 | Kramer et al. | 560/233 |
| 4,554,383 A | 11/1985 | Knifton | 568/428 |
| 5,095,141 A * | 3/1992 | Schammel et al. | 562/414 |
| 5,910,613 A | 6/1999 | Schiraldi et al. | 568/428 |

FOREIGN PATENT DOCUMENTS

| | | | |
|---|---|---|---|
| DE | 502333 | 7/1930 | |
| EP | 083224 | 7/1983 | C07C/51/265 |
| EP | 896960 | 2/1999 | C07C/51/265 |
| FR | 820545 | 11/1937 | |
| GB | 1108178 | 4/1968 | C07C/3/62 |
| GB | 1422308 | * 1/1976 | |
| GB | 2056979 | 3/1981 | C07C/63/307 |
| JP | 51146430 | 12/1976 | |
| WO | 93/24432 | 12/1993 | C07C/15/08 |

OTHER PUBLICATIONS

"Aldehyde Syntheses" G.A. Olah, et al., Friedel–Crafts and Related Reactions, Wiley–Interscience, vol. III, Chapter XXXVIII, pp. 1153–1256, 1964.

"Superacid–Catalyzed Formylation of Aromatics with Carbon Monoxide," G.A. Olah et al., J. Org. Chem., vol. 50, pp. 1483–1486, 1985.

"Aromatic Substitution, XXXIX[1] Varying Selectivity in Electrophilic Formylation of Toluene and Benzene" G.A. Olah, et al., J. Am. Chem. Soc., vol. 98, 1, pp. 296–297, Jan. 7, 1976.

* cited by examiner

Primary Examiner—Johann Richter
Assistant Examiner—Sikarl A. Witherspoon
(74) Attorney, Agent, or Firm—Lucinda Lomas

(57) ABSTRACT

A composition containing isomeric mixtures of arylaldehydes prepared from a mixed alkyl aromatic feedstock. A composition containing isomeric mixtures of dimethylbenzaldehydes prepared from a mixed xylene feedstock using a Gatterman-Koch type reaction. A composition of isomeric mixtures of tolualdehydes prepared from a toluene feedstock using a Gatterman-Koch type reaction.

6 Claims, 1 Drawing Sheet

ALKYL AROMATIC ALDEHYDES

CROSS-REFERENCE TO RELATED APPLICATIONS

Figure 1:
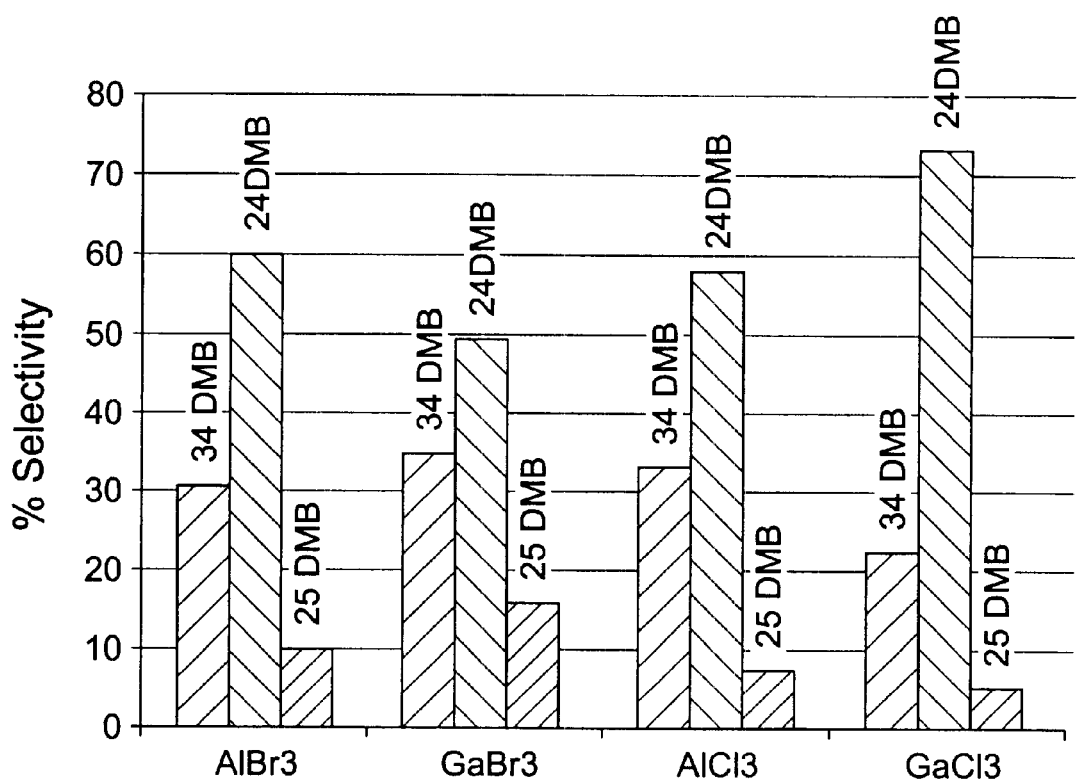

This application is a continuation in part of U.S. Ser. No. 09/393,664, filed Sep. 10, 1999, now U.S. Pat. No. 6,303,827 which claims priority to U.S. Ser. No. 60/099,783, filed Sep. 10, 1998.

FIELD OF THE INVENTION

This invention relates to compositions of alkyl aromatic aldehydes from a process for making alkyl aromatic aldehydes from the carbonylation of alkyl aromatic compounds.

BACKGROUND OF THE INVENTION

Carbonylation of an alkyl aromatic compound to form an alkyl aromatic aldehyde can be carried out by a reaction generally referred to as the Gatterman Koch reaction. Published in 1897, Gatterman and Koch described the direct carbonylation of various aromatic compounds by the use of carbon monoxide (CO) and hydrogen chloride in the presence of aluminum chloride and cuprous chloride (Gatterman, L. and Koch, J. A., *Chem. Ber.*, 30, 1622 (1897)). The reaction was subsequently expanded to include other Lewis acids. A review of such reactions is set forth in Olah, G. A., "*Friedel-Crafts and Related Reactions*", Wiley-Interscience, N.Y., Vol. 1153 (1964).

Catalysts used in a Gatterman-Koch carbonylation reaction are typically complexed with the resulting aromatic aldehyde product. To free the desired aldehyde from the acid catalyst, water is added and the resulting organic and aqueous phases separated. For example, water can be added to a tolualdehyde-$AlCl_3$ complex to obtain the aldehyde product in a complex-free form. However, this separation procedure chemically alters and destroys the utility of the catalyst. This aqueous separation method, which leads to a one time use of catalyst, renders this process commercially unattractive as catalyst regeneration and recycle would be prohibitively expensive.

U.S. Pat. No. 2,485,237, describes replacing the hydrogen chloride and aluminum chloride catalyst with a hydrogen fluoride:boron trifluoride ($HF:BF_3$) catalyst. An improved method of recovering the fluorides is described is U.S. Pat. No. 3,284,508.

A method to recycle the $HF:BF_3$ was proposed by Olah, G. A. et al., *J. Am. Chem. Soc.*, 98:1, 296 (1976). The carbonylation reaction is carried out at low temperatures, typically from 0° C. to 20° C, with excess HF. The lower boiling catalyst is separated from the aldehyde-catalyst complex by a distillation technique, condensed and returned to the carbonylation reactor. While this method is useful, it is generally desirable to have a method that avoids the use of HF, a material which requires special containment and handling facilities.

U.S. Pat. No. 3,948,998 describes a two-step process for making tolualdehyde. First, a toluene-HF—$BF_3$ complex is formed and reacted with CO to form tolualdehyde. Second, additional CO and optionally additional toluene is added to the reaction medium. Other catalysts that have been used in a Gatterman-Koch type carbonylation include combinations of Lewis and strong Bronsted acids, e.g., $SbF_5$—HF, described in U.S. Pat. No. 4,218,403. The use of Bronsted acids alone, such as fluorosulfonic acid or trifluomethane sulfonic acid, were also reported to be effective catalysts. See for example Olah, G. A. Laali, K., and Farooq, O., *J. Org. Chem.*, 50, 1483 (1985).

However, the catalysts used in Gatterman-Koch carbonylation are typically complexed with the aldehyde product. Thus a stoichiometric amount of catalyst is "consumed" in the reaction. Further, in order to obtain the aldehyde product in a complex-free form, a separation step is needed. For instance, water can be added to a tolualdehyde-$AlCl_3$ complex to obtain the aldehyde product in a complex-free-form. However, this step chemically alters and destroys the utility of the catalyst. Such a separation, which leads to a one time use of the catalyst renders this process commercially unattractive as catalyst regeneration and recycle would be prohibitively expensive.

SUMMARY OF THE INVENTION

An aromatic aldehyde composition containing isomeric mixtures of dimethylbenzaldehydes prepared from contacting a mixed xylene feedstock with a carbonylation catalyst using a Gatterman-Koch type reaction. The aromatic aldehyde composition contains from about 80% to about 96% by weight, preferably from about 90% to about 96% by weight, 2,4-dimethylbenzylaldehyde, from about 2% to about 15% by weight, preferably from about 2% to about 6% by weight, 3,4-dimethylbenzylaldehyde, less than about 3% by weight 2,5-dimethylbenzylaldehyde, and less than about 3% by weight 4-ethyllbenzylaldehyde. This aromatic aldehyde composition can then be oxidized using known methods to form an aromatic acid composition containing about 80% to about 98% by weight trimellitic acid and about 2% to about 10% by weight terephthalic acid.

The carbonylation catalyst used in the Gatterman-Koch type reaction is selected from perfluoroalkyl sulfonic acids with about 2 to about 18 carbon atoms, perfluoroether sulfonic acids with about 2 to about 18 carbon atoms, $GaBr_3$, $GaCl_3$, $AlBr_3$, $AlCl_{13}$, $AlI_3$, $TaF_5$, $NbF_5$, or $NbBr_5$. Preferably, the carbonylation catalyst is selected from perfluorohexane sulfonic acid, perfluorooctane sulfonic acid, and perfluoroethoxyethane sulfonic acid.

The invention is further directed to a composition of isomeric mixtures of tolualdehydes prepared from contacting a toluene feedstock with a carbonylation catalyst using a Gatterman-Koch type reaction. The composition contains about 85% to about 97% by weight para-tolualdehyde, about 2% to about 10% by weight ortho-tolualdehyde, and about 2% by weight or less, preferably about 1% by weight or less, more preferably about 0.5% by weight or less, meta-tolualdehyde. This aromatic aldehyde composition can then be oxidized using known methods to form an aromatic acid composition containing about 80% to about 98% by weight terephthalic acid, about 2% to about 10% by weight phthalic acid, and less than about 3% by weight isophthalic acid.

DETAILED DESCRIPTION OF THE INVENTION

This invention is directed to compositional mixtures of alkyl aromatic aldehydes. The alkyl aromatic aldehyde compositions of the invention are produced from contacting an alkyl aromatic feed with a carbonylation catalyst. The alkyl aromatic aldehyde compositions can contain two or more of the following alkyl aromatic compounds: ortho-tolualdehyde, meta-tolualdehyde, para-tolualdehyde, 2,4-dimethylbenzaldehyde (2,4-DMB), 3,4-dimethylbenzaldehyde (3,4-DMB), 2,5-dimethylbenzaldehyde (2,5-DMB), 2,4,5,-trimethylbenzaldehyde, 4-ethylbenzaldehyde, 4-propylbenzaldehyde, and 4-isopropylbenzaldehyde. The tolualdehyde compositions are formed if toluene is used as the aromatic aldehyde feedstock. The dimethylbenzaldehydes and the higher 4-alkylbenzaldehydes are formed if a feedstock containing primarily mixed xylenes is used as a feedstock.

The alkyl aromatic aldehyde compositions can also contain a mixture of alkyl-substituted benzaldehydes, wherein the alkyl groups include, but are not limited to, are selected from methyl, ethyl, propyl, isopropyl, or butyl. These alkyl benzaldehyde compositions result from the reaction of an alkyl aromatic feedstock, containing at least three alkyl aromatic compounds, with carbon monoxide in the presence of a high boiling point carbonylation catalyst. The alkyl aromatic feedstocks that can be used to provide the alkyl-substituted benzaldehyde compositions include, but are not limited to, at least three of the following compounds selected from 1-methyl-3-propylbenzene, 1-methyl-2-propylbenzene, 1,4-diethylbenzene, 1-methyl-4-propylbenzene, butylbenzene, 2-ethyl-1,4-dimethylbenzene, 4-ethyl-1,2-dimethylbenzene, 1-ethyl-2,4-dimethylbenzene, 1,2,4,5-tetramethylbenzene, and 1,2,3,5-tetramethylbenzene.

These alkyl aromatic feedstocks can be defined by an average boiling point of the alkyl aromatic feedstock. The average boiling point is defined by the summation of the wt % of each alkyl aromatic compound in the mixture multiplied by its respective boiling point. In one embodiment, the average boiling point of the alkyl aromatic feedstock is from about 140° C. to about 170° C., preferably from about 140° C. to about 160° C.

The alkyl aromatic aldehyde compositions can also contain a mixture of alkyl-substituted napthylaldehydes. These napthylaldehyde compositions result from the reaction of an alkyl-substituted napthalene containing feedstock, containing at least two alkyl-substituted napthalene compounds, with carbon monoxide in the presence of a high boiling point carbonylation catalyst. The alkyl-substituted napthalene feedstocks that can be used to provide the alkyl napthylaldehydes include at least two of the following compounds selected from 1-methylnapthalene, 2-methylnapthalene, 2,6-dimethylnapthalene, 2,7-dimethylnapthalene, 1,3-dimethylnapthalene, 1,5-dimethylnapthalene, 1,6-dimethylnapthalene, and 2-ethylnapthalene.

The alkyl aromatic compositions may comprise at least three of ethyldimethylbenzaldehye; methylpropylbenzaldehyde; diethyl-, propylethyl-, and trimethyl-benzaldehydes, trimethylbenzaldehyde, naphthaldehyde, diethylbenzaldehyde, and butylbenzaldehyde. One embodiment comprises about 32% to about 33% by weight ethyldimethylbenzaldehyde, about 18% to about 20% by weight methylpropylbenzaldehyde, about 20% to about 22% by weight diethyl- and propyl-ethylbenzaldehyde, about 18% to about 20% by weight trimethylbenzaldehydes, about 9% to about 10% by weight napthaldehyde, and about 0.5% to about 1% by weight butylbenzaldehyde.

The alkyl aromatic aldehyde compositions may comprise at least two of methylnaphthaldehyde, dimethylnaphthaldehyde, naphthaldehyde, ethylnaphthaldehyde, indanecarboxaldehyde, and dimethylindanecarboxaldehyde. One embodiment comprises about 50% to about 52% by weight methylpropylaldehyde, about 25% to about 28% by weight dimethylnaphthaldehyde, about 11% to about 12% by weight naphthaldehyde, about 7% to about 8% by weight ethylnaphthaldehyde, and from about 5% to about 6% by weight indanecarboxaldehyde and dimethylindanecarboxaldehyde.

These alkyl-substituted napthalene feedstocks can be defined by an average boiling point of the alkyl-substituted napthalene feedstock. The average boiling point is defined by the summation of the wt % of each alkyl napthalene compound in the mixture multiplied by its respective boiling point. In one embodiment, the average boiling point of the alkyl-substituted napthelene feedstock is from about 170° C. to about 220° C., preferably from about 180° C. to about 210° C.

A select fraction of the alkyl aromatic aldehyde compositions, particularly the dialkyl and trialkyl aromatic aldehydes can be oxidized to the corresponding trimellitic acid and pyromellitic acid. These compounds can further undergo dehydration to form the corresponding anhydrides. Similarly, the para-tolualdehyde can be oxidized to terephthalic acid. The polycarboxylic acids are widely used as raw materials for alkyd resins, high grade plasticizer, and polyamide-imide polyester.

A "carbonylation catalyst" is defined as any compound or mixture of compounds that can catalyze the reaction of alkyl aromatic compounds with CO to form alkyl aromatic aldehydes. Generally, carbonylation catalysts are Lewis and/or Bronsted acids.

One embodiment of the invention is directed to an alkyl aromatic composition containing dimethylbenzaldehydes prepared from a mixed xylene feedstock using a Gatterman-Koch type reaction. The composition is obtained by reacting a mixed xylene feedstock with carbon monoxide in the presence of a carbonylation catalyst to form an aromatic aldehyde-catalyst complex. The aromatic aldehyde composition is then separated from the carbonylation catalyst. The catalyst can then be recycled to the carbonylation reaction.

This invention is also directed to a composition of isomeric mixtures of tolualdehydes prepared from a toluene feedstock using a Gatterman-Koch type reaction. The composition is obtained by reacting toluene with carbon monoxide in the presence of a carbonylation catalyst to form a tolualdehyde-catalyst complex. The tolualdehyde composition is then separated from the carbonylation catalyst by selectively volatilizing the tolualdehydes. The catalyst can then be recycled to the carbonylation reaction.

"High boiling point carbonylation catalyst" means a carbonylation catalyst that has a boiling point that is higher than the desired aromatic aldehyde to be produced. Typically, the high boiling point carbonylation catalyst has a boiling point of at least about 210° C., preferably at least about 230° C., and more preferably at least about 250° C. The high boiling point catalyst can be in liquid or solid form, the latter including supported and unsupported catalysts. Suitable support materials are, in general, well known in the catalyst art and include zeolites, ceramics and polymeric supports. A high boiling point carbonylation catalyst includes solid and supported catalysts that do not boil per se, but rather melt or degrade at high temperatures. These types of catalysts have a boiling point above their melting/degrading temperatures. So long as the aldehyde product can be distilled from the carbonylation catalyst, the unsupported catalyst and the solid or supported catalyst is within the scope of a high boiling point carbonylation catalyst. The term distilled is defined as separating the more volatile components of a mixture by the condensation of the vapors that are produced as the mixture is heated at atmospheric, sub-atmospheric, or super atmospheric pressure. Specific high boiling point carbonylation catalysts that can be used in the invention include perfluoroalkyl sulfonic acids having about 2 to about 18 carbon atoms, perfluoroether sulfonic acids having about 2 to about 18 carbon atoms, $GaBr_3$, $GaCl_3$, $AlBr_3$, $AlCl_3$, $AlI_3$, $TaF_5$, $NbF_5$, and $NbBr_5$.

The perfluoroalkyl sulfonic acids include compounds of the formula $R_fSO_3H$ wherein $R_f$ is a straight or branched chain perfluoroalkyl group having about 2 to about 18 carbon atoms, preferably about 2 to about 8 carbon atoms. Examples of such carbonylation catalysts include, but are not limited to, perfluoroethane sulfonic acid, perfluorobutane sulfonic acid, perfluorohexane sulfonic acid and perfluorooctane sulfonic acid.

The perfluoroether sulfonic acids are typically of the formula $R_1OR_2SO_3H$ wherein $R_1$ and $R_2$ each represent a straight or branched chain perfluoroalkyl group having about 1 to about 10 carbon atoms, preferably about 1 to about 4 carbon atoms. Acids of this type include compounds, or mixtures of compounds, of the formula $CF_3(CF_2)_z O(CF_2)_y SO_3H$ wherein z and y are each independently a number from about 1 to about 3. An example of a perfluoroether sulfonic acid carbonylation catalyst is perfluoroethoxyethane sulfonic acid (y=2, z=1).

It should be understood that the carbonylation catalyst compounds described herein are used with their conventional meanings and thus include all variations of the compounds, including ionic and complexed forms, as can occur in situ. For example, in the presence of protons, the Lewis acid $AlCl_3$ is believed to form $H^+$ and $AlCl_4^-$. Further, the $AlCl_4^-$ can combine with $AlCl_3$ to form $Al_2Cl_7^-$ and higher homologues. Recognizing that in situ changes can occur to the "catalyst" compound, including complexing reactions or rearrangements all such forms and variations are collectively embraced by reference to the catalyst supplied to the reaction system. Thus, for example, identifying the catalyst as $AlCl_3$ embraces carrying out the carbonylation reaction in the presence of any of $AlCl_3$, $AlCl_4^-$, $AlCl_7^-$ and/or higher homologues thereof.

It is preferred that the carbonylation reaction be carried out in the absence of any added HF. This means that no effort is taken to add HF to the reaction system. However, HF can be present in the feeds as an impurity. Similarly, HF can be created in situ when a fluoride-containing compound is present. Such in situ formation does not correspond to "added HF."

The alkyl aromatic compounds that can be converted to the corresponding aromatic aldehydes in the invention include, but are not limited to, hydrocarbon aromatic ring compounds having one or more $C_1$–$C_4$ alkyl substituents. Generally the alkyl aromatic compounds are substituted benzenes having 1 to 3 alkyl groups. Examples of alkyl aromatic compounds include toluene, ortho- (o-), meta- (m-) and para- (p-) xylenes, ethylbenzene, pseudocumene (1,2, 4-trimethylbenzene), mesitylene (1,3,5-trimethylbenzene), propylbenzene, and isopropylbenzene.

The alkyl aromatic compound is converted to the corresponding alkyl aromatic aldehyde as a result of the carbonylation reaction. The formyl group is directly bonded to the aromatic ring. The reaction of toluene with carbon monoxide (CO) under carbonylation conditions produces an aromatic aldehyde composition containing all three isomers; p-tolualdehyde, o-tolualdehyde, and m-tolualdehyde. Preferably, the aldehyde aromatic composition contains at least about 85% p-tolualdehyde, depending upon the catalyst, the reaction temperature, and reaction pressure. The o-tolualdehyde is produced in amounts from about 2% to about 10% by weight. The m-tolualdehyde is typically produced in amounts of about 2% by weight or less, preferably about 1% by weight or less, more preferably about 0.5% by weight or less.

The reaction of mixed xylenes with CO under carbonylation conditions of the invention produces three DMB isomers, that is, 2,4-DMB, 3,4-DMB, and 2,5-DMB, as well as 4-ethylbenzaldehyde. The product ratio 4-ethylbenzaldehyde:2,5-dimethylbenzene is typically from about 2:1 to about 1:3. The 4-ethylbenzaldehyde results from the reaction of 4-ethylbenzene, which is often, if not always present in mixed xylenes. Typically, mixed xylenes contain from about 10% to about 30% by weight 4-ethylbenzene.

Mixed xylenes are defined as an aromatic composition containing o-xylene, p-xylene, m-xylene, and 4-ethylbenzene. The mixed xylenes can also contain other hydrocarbons. Generally, these hydrocarbons will have a boiling point between about 120° C. and about 160° C. The mixed xylenes will contain from about 30% to about 75% m-xylene, from about 5% to about 30% o-xylene, from about 2% to about 20% p-xylene, and from about 5% to about 35% ethylbenzene.

FIG. 1 shows the relative product selectivity of a synthetic mixed xylene feed prepared without 4-ethylbenzene for the Lewis acid catalysts shown. Approximately, equal proportions of each isomeric xylene by weight were contained in the feed. As suggested by the isomeric product distribution of DMBs in FIG. 1, m-xylene is more reactive than o-xylene, which is more reactive than pxylene, under the carbonylation reaction conditions of the invention. The reactivity depends upon the carbonylation catalyst used. $GaCl_3$ exhibits the highest selectivity to 2,4-DMB.

The carbonylation reaction is typically carried out by combining the carbonylation catalyst, optionally a solvent, a gas containing carbon monoxide, and the alkyl aromatic compound in a reactor. The carbonylation catalyst can be combined or dissolved with the alkyl aromatic compound to form a solution or a slurry. The latter is formed if a solid carbonylation catalyst is used. The reaction can be carried out in either batch, semi-batch, or continuous fashion.

The amount of carbonylation catalyst is not particularly limited and is generally equal to at least about one half of the molar amount of alkyl aromatic compound, typically from about 0.5 to about 20 times the molar amount of alkyl aromatic compound. For a Bronsted acid catalyst such as the perfluoroalkyl sulfonic acids, it is preferred that the catalyst be provided in molar excess to the alkyl aromatic compound, preferably from about 6 to about 20 molar excess, more preferably from about 6 to about 12 molar excess of carbonylation catalyst. In general, higher Bronsted acid catalyst concentrations provide for higher conversion. For a Lewis acid catalyst such as aluminum halides and gallium halides, it is preferred that the carbonylation catalyst be provided in molar amounts of about 0.08 to about 1.5 times the molar amount of alkyl aromatic compound. Preferably, the Lewis acid catalyst is provided in about or slightly in excess of about a 1:1 molar ratio to the alkyl aromatic compound.

The carbonylation reaction is generally carried out at a pressure from about 0 kg/cm$^2$ to about 300 kg/cm$^2$ (gauge), preferably from about 15 kg/cm$^2$ to about 200 kg/cm$^2$ (gauge), more preferably from about 4 kg/cm$^2$ to about 100 kg/cm$^2$ (gauge), and most preferably from about 4 kg/cm$^2$ to about 25 kg/cm$^2$ (gauge). Generally, an increase in pressure increases the cost of the reaction and/or the equipment and must be balanced against the increased productivity, if any. The use of a lower reaction pressure can be facilitated by incorporating co-catalysts, such as copper oxide or silver oxide into the reaction mixture. These co-catalysts can be used to improve the conversion rate at lower reaction pressures and/or lower temperatures.

Specifically, cuprous chloride, as was used in the original Gatterman-Koch reaction, copper oxide or silver oxide, as are described in U.S. Pat. No. 4,518,798 can each be used to improve the conversion rate at lower reaction pressures and/or more mild overall reaction conditions. Other metal salts as are known in the art for carbonylation can also be used.

The presence of $CO_2$ or $H_2$ in the carbon monoxide gas does not generally affect the carbonylation reaction. Accordingly, synthesis gas, which is comprised of CO, $H_2$, and optionally $CO_2$ in varying proportions, can be used as a source of CO. A stoichiometric excess of CO is generally introduced to the reactor. The CO partial pressure in the reactor is from about 0 kg/cm$^2$ to about 200 kg/cm$^2$ (gauge), preferably from about 1 kg/cm$^2$ to about 100 kg/cm$^2$ (gauge), and more preferably from about 2 kg/cm$^2$ to about 25 kg/cm$^2$ (gauge). The amount of CO is generally at least about 20 mol % of the gas supplied. For example, synthesis gas can vary from a CO:$H_2$ molar ratio of about 1:1 to about 1:3. Further $CO_2$ can also be present in amounts of up to about 30 mol %. Of course, the gas supplied to the reactor can be 100% CO.

The carbonylation reaction can be carried out over a wide range of temperatures. Usually the reaction temperature is within the range of from about 0° C. to about 175° C. more typically within the range of from about 0° C. to about 100° C. such as from about 0° C. to about 50° C. The temperature of the carbonylation reaction will depend upon the reaction conditions, the alkyl aromatic feed, the desired aromatic aldehyde composition, and the carbonylation catalyst used.

The carbonylation reaction is carried out for a sufficient time to achieve the desired product or conversion under the conditions employed. Generally the reaction is run for about 0.1 to about 5 hours although longer or shorter times can be used depending upon the reaction conditions, the alkyl aromatic feed, the desired aromatic aldehyde composition, and the carbonylation catalyst used.

In one embodiment, which takes advantage of the relatively high boiling point of the carbonylation catalyst, the aromatic aldehyde composition is separated from the resulting aldehyde-catalyst complex by selectively volatilizing the aldehyde composition from the aldehyde-catalyst complex. The aldehyde composition is volatized without substantial degradation. It is preferred that no more than about 30% by weight, more preferably no more than about 10% by weight, of the aldehyde composition resulting from the carbonylation reaction degrade during the selective volatilization separation.

The volatilization technique used should achieve separation in a short time period in order to avoid unwanted side reactions and/or degradation that are prone to occur in heating the aromatic aldehyde-catalyst complex over an extended period at high temperatures. Generally, the volatilization technique has a liquid residence time of less than about 5 minutes, preferably less than about 3 minutes, more preferably less than about 1 minute. Suitable techniques include evaporation, vaporization, flash distillation and combinations thereof. As is well understood, increasing the temperature and/or decreasing the pressure will increase the rate of volatilization. Desirably, the temperature used to volatilize the desired aldehyde is from about 90° C. to about 350° C., preferably from about 90° C. to about 250° C., more preferably from about 90° C. to about 200° C.

The term "selectively volatilizing" means that the volatilizing technique preferably volatilizes the desired aromatic aldehyde, and little, if any, of the high boiling point carbonylation catalyst. This leads to an aromatic aldehyde-rich vapor and a carbonylation catalyst-rich liquid. However, a perfect separation of the aromatic aldehyde from the high boiling point carbonylation catalyst is generally not possible because the high boiling point carbonylation catalyst is likely to have some vapor pressure. As a result, the aromatic aldehyde-rich vapor will contain some amount of high boiling point carbonylation catalyst. Accordingly, for purposes of the invention, the separation is considered to be selective for the aromatic aldehyde if less than about 50%, preferably less than about 30%, and more preferably less than about 15%, of the high boiling point carbonylation catalyst is present in the resulting aromatic aldehyde-rich vapor.

One way to selectively volatilize the aromatic aldehyde is to use a wiped-film evaporator, sometimes referred to as an agitated film evaporator. This volatilization unit is generally comprised of a straight or tapered tube containing concentric, rotating paddles. The edge of the paddles can be in or above the film layer. The liquid, aromatic aldehyde-catalyst complex is directed to the interior surface of the tube as a thin film. The paddles are rotated to aid in the formation of the desired film thickness. The wall of the tube is normally heated. The volatilized aromatic aldehyde is directed to the annular region of the tube and removed as a vapor. The process can be run at a variety of pressures, but is preferably carried out under reduced pressure. The wall temperature is typically at least about 90° C., and is usually in the range of about 90° C. to about 350° C. It should be noted that the lower temperatures, i.e. those less than about 200° C., are sufficient to volatilize the aromatic aldehyde provided the pressure is sufficiently low. To increase the separation efficiency, regardless of the temperature, it is preferred that the pressure is less than or equal to about 0.5 kg/cm$^2$ (gauge), more preferably less than about 0.1 kg/cm$^2$ (gauge). The condensate contains the aromatic aldehyde and unreacted alkyl aromatic compounds while the majority or all or substantially all of the carbonylation catalyst remains in the liquid film. The high boiling point carbonylation catalyst can then be recycled to the carbonylation reactor.

Another way to selectively volatilize the aromatic aldehyde is to use a flash distillation unit. The aromatic aldehyde-catalyst complex from the carbonylation reactor is sent to a flash chamber where a portion of the aromatic aldehyde product is volatilized. The majority or all or substantially all of the high boiling point carbonylation catalyst remains in the liquid phase and exits as a bottom stream. The high boiling point carbonylation catalyst can then be recycled to the carbonylation reactor. The vapor or distillate containing the aromatic aldehyde product and unreacted alkyl aromatic compounds is condensed. The aromatic aldehyde is then further separated from the unreacted aromatic compounds. The unreacted aromatic compounds can then be recycled to the carbonylation reactor.

As previously stated, it is preferred that the separation of the aromatic aldehyde from the high boiling point carbonylation catalyst occur relatively rapidly so as to avoid degradation of the desired aromatic aldehyde product. One way this can be achieved is to heat the liquid phase in a heat exchanger very quickly just prior to introducing the liquid, aromatic aldehyde-catalyst complex to the flash chamber. The temperature is preferably increased to at least about 200° C., more preferably within the range from about 230° C. to about 300° C., in less than about 4 minutes, preferably less than about 2 minutes, more preferably in less than about 20 seconds. The rapidly heated complex is then supplied to the flash chamber where the more volatile aromatic aldehyde products and unreacted aromatic compounds are separated from the high boiling point carbonylation catalyst. Under these conditions, the aromatic aldehyde will begin to vaporize in the heat exchanger before reaching the flash chamber, thereby reducing the average aldehyde-catalyst contact time at the higher temperatures in the flash chamber. The residence time of the complex in the flash chamber is typically about 10 seconds or less, preferably about 5 seconds or less, for the liquid and generally about 5 seconds or less, preferably about 5 seconds or less, for the volatilized compounds.

After the flash volatillization, the vapor is preferably subjected to an absorbing tower or other suitable unit to remove any remaining high boiling point carbonylation catalyst in the vapor. For example, the vapor can be run through a multi-plate column where a diluent, e.g. toluene, is added. Preferably, the diluent is added in a counter-current direction. The high boiling point carbonylation catalyst, if any, will re-complex with the aromatic aldehyde and rapidly condense out of the vapor. This leaves a vapor with the desired aromatic aldehyde and excess diluent and/or aromatic alkyl compound with essentially no high boiling point carbonylation catalyst. The liquid stream containing the aldehyde-catalyst complex can be recycled back to the heat exchanger and flash chamber. Such an absorbing column is preferably used with the flash separation technique, but is suitable for use with any selective volatilization method.

The separated alkyl aromatic aldehydes can then be oxidized to form the corresponding aromatic acids using methods known in the art. The aromatic acids can then be dehydrated to the corresponding anhydrides using methods known in the art. In general, oxidation comprises combining the aromatic aldehyde with oxygen or an oxygen containing gaseous mixture, optionally in the presence of an oxidation catalyst. A solvent such as a lower aliphatic acid, an ester, or water is typically used in an oxidation reaction. Examples of solvents include, but are not limited to, formic acid, acetic acid, propionic acid, n-butyric acid, iso-butyric acid, valeric acid, trimethylacetic acid, caproic acid, methyl benzoate, dimethyl terephthalate, and water.

The oxidation catalysts are well known and include cobalt salts, manganese salts, chromium salts, lanthanide salts especially cerium salts, and mixtures thereof. Examples of catalysts include cobalt acetate or naphthenate, and manganese acetate or naphthenate. A combination of Co/Mn is particularly preferred as a catalyst. The amount of catalyst is not particularly limited and is generally within the range from about 50 ppm to about 1000 ppm for managese and about 50 ppm to about 2000 ppm for cobalt, based on the solvent. Bromine or other free radical initiators can optionally be included to aid in the reaction. However, because the oxidation is carried out with an aldehyde, free radical initiators such as HBr can be advantageously minimized or omitted. Further, in view of its corrosive nature, bromine, or progenitor thereof, is preferably excluded from the oxidation reaction or minimized as is described in U.S. Pat. No. 5,453,538.

Oxygen used in the oxidation reaction can be supplied to the reactor as pure oxygen or as a mixed gas containing other inert gases such as nitrogen. Thus, air can be used as an oxidizing gas. The oxidation reaction is preferably conducted at a pressure from about 0 kg/cm$^2$ to about 35 kg/cm$^2$ (gauge), more preferably from about 10 kg/cm$^2$ to about 30 kg/cm$^2$ (gauge). The oxidation reaction temperature is generally within the range from about 100° C. to about 252° C., more typically from about 120° C. to about 240° C.

The aromatic aldehyde compositions of the invention can be converted to the corresponding acids or anhydrides. For example, p-tolualdehyde produced from the carbonylation of toluene can be oxidized to terephthalic acid. The 4-ethylbenzaldehyde produced in the carbonylation of the mixed xylenes can also be oxidized to terephthalic acid.

Once separated from the produced 4-ethylbenzaldehyde, the dimethylbenzaldehydes produced from the mixed xylenes can be oxidized to form trimellitic acid. The trimellitic acid can then be dehydrated to form trimellitic anhydride. Thus, trimellitic anhydride can be produced from a mixed xylene feed without the need to isolate a particular isomer of the mixed xylene feed.

Alternatively, the aromatic aldehyde product from the carbonylation of mixed xylenes can be directed to an oxidation unit without prior separation of 4-ethylbenzaldehyde. The resulting aromatic acid composition should contain about 80% to about 98% by weight trimellitic acid from the oxidation of the dimethylbenzaldehydes and about 2% to about 10% by weight terephthalic acid from the oxidation of 4-ethylbenzaldehyde.

Other alkyl aromatic aldehydes produced according to the invention can also be oxidized to form the corresponding aromatic acids. For example, pyromellitic acid can be produced from 2,4,5-trimethylbenzaldehyde which is obtained by carbonylating pseudocumene. The pyromellitic acid can then be dehydrated to form pyromellitic dianhydride. Likewise, mesitaldehyde can be oxidized to form trimethyl benzoic acid.

The following non-limiting examples are provided in order to further demonstrate the various embodiments and advantages of the invention.

EXAMPLE 1

Perfluorooctanesulfonic acid (8 grams) and toluene (3 mL) were charged to a Hastelloy C minireactor tube equipped with two valves. The reactor was pressurized with CO to 1050 psig, sealed, placed in a shaker-mounted heated block, and shaken at 50° C. for two hours. The reactor was quickly cooled to room temperature and vented. The contents were poured into ice water, and the organic layer was extracted with diethyl ether. Analysis by gas chromatography showed about 2% conversion of the toluene. The product isomer distribution was 93% para-tolualdehyde, 7% ortho-tolualdehyde, and no meta-tolualdehyde.

EXAMPLE 2

The procedures of Example 1 were followed except that perfluorohexanesulfonic acid (6 gram) and toluene (3 mL) were charged to the reactor. Analysis by gas chromatography showed about 2% conversion of the toluene. The product isomer distribution was again 93% para-tolualdehyde, 7% ortho-tolualdehyde, and no meta tolualdehyde.

EXAMPLE 3

The procedures of Example 1 were followed except that perfluoroethoxyethanesulfonic acid (7 grams) and toluene (3 mL) were charged to the reactor and the reactor was not heated. Analysis by gas chromatography showed about 9% conversion of the toluene. The product isomer distribution was again 93% para-tolualdehyde, 7% ortho-tolualdehyde, and no meta-tolualdehyde.

EXAMPLE 4

The procedures of Example 1 were followed except that trifluoroacetic acid (7 grams) and toluene (3 ML) were charged to the reactor and the reactor was not heated. No product aldehydes were found.

EXAMPLE 5

This Example demonstrates separation of the acid catalyst from the aldehyde product. The complex of perfluorohexanesulfonic acid with para-tolualdehyde (26 grams) was dissolved in trifluoroacetic acid (53 grams). This solution was fed to a wiped film evaporator apparatus over a period of 20 minutes. The evaporator was run with a wall temperature of 100° C. under a pressure of 0.25 mmHg. The material that collected on the cold finger of the evaporator was analyzed by gas chromatography and found to be para-tolualdehyde. The perfluorohexanesulfonic acid was non-volatile (boiling point 260° C.) and was collected at the bottom of the evaporator. The trifluoroacetic acid solvent also volatilized and was collected in a dry ice trap.

EXAMPLE 6

This Example demonstrates that the trifluoromethanesulfonic (triflic) acid catalyst cannot be selectively separated from the para-tolualdehyde by volatilization.

A complex of triflic acid with para-tolualdehyde (130 grams) was fed to a wiped film evaporator apparatus over a period of 40 minutes. The evaporator was run with a wall temperature of 115° C. under a pressure of 0.4 mmHg. The material that collected on the cold finger of the evaporator (about 105 grams) was identified as triflic acid. The non-volatile fraction was collected at the bottom of the evaporator as a dark black, viscous liquid that was soluble in toluene. GC analysis of this heavy fraction showed mainly higher boiling products and no para-tolualdehyde.

EXAMPLE 7

In a manner similar to Example 1, toluene and $GaBr_3$ were supplied to a reactor to form a reaction mixture having a ratio of 0.2 mol $GaBr_3$/mol toluene. The reactor was pressurized with CO to 1100 psig and run for one hour at room temperature. Analysis showed about 20% conversion of the toluene. The product isomer distribution was 91% para-tolualdehyde, 8% ortho-tolualdehyde, and 1% meta-tolualdehyde.

EXAMPLE 8

In a manner similar to Example 1, mixed xylenes (32.5% para, 32.5% meta, 35% ortho and $GaBr_3$ were supplied to a reactor to form a reaction mixture having a ratio of 0.2 mol $GaBr_3$/mol xylenes. The reactor was pressurized with CO to 1100 psig and run for one hour at room temperature. Analysis showed about 22% conversion of the xylenes. The product isomer distribution was 21.2% 3,4-dimethylbenzaldehyde, 74.8% 2,4-dimethylbenzaldehyde, and 4.1% 2,5-dimethylbenzaldehyde.

EXAMPLE 9

$GaCl_3$ and toluene were charged to a 500 cc stirred autoclave in a $GaCl_3$: toluene molar ratio of 0.16. The reaction was run at varying CO pressures and temperatures and samples were withdrawn at various times and analyzed. After about 3 hours at a temperature of 25° C. to 26° C. and under a CO pressure of 1068 to 1077 psig, 15.6% of the toluene had been converted to tolualdehyde. The product isomer distribution was 88.8% para-tolualdehyde, 10.3% ortho-tolualdehyde, and 0.9 meta-tolualdehyde. The CO pressure was then increased to the range of around 1536 to 1549 psig and measurements at 7.08 hours from start showed 16.9% conversion. The product isomer distribution was 88.2% para-tolualdehyde, 10.7% ortho-tolualdehyde, and 1.1% meta-tolualdehyde.

The invention having been thus described, it will be obvious that the same can be varied in many ways without departing from the spirit and scope of the invention as defined by the following claims.

What is claimed is:

1. An aromatic acid composition comprising:
   about 80% to about 98% by weight terephthalic acid;
   about 2% to about 10% by weight phthalic acid; and
   less than about 3% by weight isophthalic acid.

2. An aromatic acid composition comprising:
   about 80% to about 98% by weight trimellitic acid; and
   about 2% to about 10% by weight terephthalic acid.

3. An alkyl benzaldehyde composition comprising:
   about 32% to about 33% by weight ethyldimethylbenzylaldehyde;
   about 18% to about 20% by weight methylpropylbenzylaldehyde; and
   about 20% to about 22% by weight diethyl- and propylethylbenzylaldehyde;
   about 9% to about 10% naphthaldehyde; and
   about 0.5% to about 1% butylbenzaldehye; wherein the alkyl benzaldehyde composition is produced from contacting an alkyl benzene feedstock with a carbonylation catalyst.

4. The alkyl benzaldehyde composition of claim 3, wherein at least one carbonylation catalyst is selected from perfluoroalkyl sulfonic acids with about 2 to about 18 carbon atoms, perfluoroether sulfonic acids with about 2 to about 18 carbon atoms, $GaBr_3$, $GaCl_3$, $AlBr_3$, $AlCl_3$, $AlI_3$, $TaF_5$, $NbF_5$, and $NbBr_5$.

5. An alkyl napthylaldehyde composition comprising:
   about 50% to about 52% by weight methylnapthylaldehyde;
   about 25% to about 28% by weight dimethylnapthylaldehyde;
   about 11% to about 12% by weight napthaldehyde;
   about 7% to about 8% by weight ethylnapthaldehyde; and
   about 5% to about 6% by weight indanecarboxaldehyde and dimethylindanecarboxaldehyde; wherein the alkyl napthylaldehyde composition is produced from contacting an alkyl napthalene feedstock with a high boiling point carbonylation catalyst.

6. The alkyl napthylaldehyde composition of claim 5, wherein at least one carbonylation catalyst is selected from perfluoroalkyl sulfonic acids with about 2 to about 18 carbon atoms, perfluoroether sulfonic acids with about 2 to about 18 carbon atoms, $GaBr_3$, $GaCl_3$, $AlBr_3$, $AlCl_3$, $AlI_3$, $TaF_5$, $NbF_5$, and $NbBr_5$.

* * * * *